US006977180B2

(12) United States Patent
Hellinga et al.

(10) Patent No.: US 6,977,180 B2
(45) Date of Patent: Dec. 20, 2005

(54) BIOSENSOR

(75) Inventors: Homme W. Hellinga, Durham, NC (US); David W. Conrad, Durham, NC (US); David E. Benson, Ferndale, MI (US)

(73) Assignee: Duke University, Durham, NC (US)

( * ) Notice: Subject to any disclaimer, the term of this patent is extended or adjusted under 35 U.S.C. 154(b) by 254 days.

(21) Appl. No.: 10/229,286

(22) Filed: Aug. 28, 2002

(65) Prior Publication Data
US 2003/0129622 A1 Jul. 10, 2003

Related U.S. Application Data

(60) Provisional application No. 60/315,036, filed on Aug. 28, 2001.

(51) Int. Cl.[7] ........................................... G01N 33/543
(52) U.S. Cl. ..................... 436/518; 204/400; 204/403; 422/82.01; 422/82.02; 422/82.03; 435/5; 435/6; 435/7.2; 435/7.31; 435/14; 435/287.1; 435/287.2; 436/149; 436/524; 436/525; 436/806; 436/815
(58) Field of Search ............................. 204/400, 403; 422/82.01, 82.02, 82.03; 435/5, 6, 7.31, 7.2, 435/14, 287.1, 287.2; 436/518, 524, 525, 436/149, 806, 815

(56) References Cited

U.S. PATENT DOCUMENTS

| 6,096,497 | A | 8/2000 | Bauer |
| 6,130,037 | A | 10/2000 | Lennox et al. |
| 6,197,534 | B1 | 3/2001 | Lakowicz et al. |
| 6,231,733 | B1 | 5/2001 | Nilsson et al. |
| 6,248,229 | B1 | 6/2001 | Meade |
| 6,277,627 | B1 | 8/2001 | Hellinga |
| 6,432,723 | B1 * | 8/2002 | Plaxco et al. ............... 436/518 |
| 6,521,446 | B2 | 2/2003 | Hellinga |

OTHER PUBLICATIONS

Benson et al, "Design of Bioelectronic Interfaces by Exploiting Hinge-Bending Motions in Proteins", Science, vol. 293, Aug. 31, 2001, pp. 1641-1644.*

Tolosa et al, "Glucose sensor for low-cost lifetime-based sensing using a genetically engineered protein", Anal. Biochem. 267(1):114-120 (1999)—Abstract.

Bontidean et al, "Detection of Heavy Metal Ions at Femtomolar Levels Using Protein-Based Biosensors", Anal. Chem. 70:4162-4169 (1998).

Li et al, "Comparative stereochemical analysis of glucose-binding proteins for rational design of glucose-specific agents", J. Biomater. Sci. Polymer Edn, 9(4):327-344 (1998).

Wilkins and Atanasov, "Glucose monitoring: state of the art and future possibilities", Med. Eng. Phys. 18(4):273-288 (1996).

Pickup, "Developing glucose sensors for n vivo use", Trends in Biochech. 11:285-291 (1993).

Marvin et al, "The rational design of allosteric interactions in a monomeric protein and its applications to the construction of biosensors", Proc. Natl. Acad. Sci. USA 94:4366-4371 (1997).

(Continued)

Primary Examiner—Christopher L. Chin
(74) Attorney, Agent, or Firm—Nixon & Vanderhye P.C.

(57) ABSTRACT

The present invention relates, in general, to biosensors and, in particular, to bioelectronic sensors comprising a macromolecule immobilized on an electrode surface so that a redox cofactor that is site-specifically attached to the surface of the macromolecule is between the macromolecule and electrode surface ligand-mediated conformational changes alter the geometry of interaction between the redox cofactor and the electrode surface resulting in a change in electronic coupling between the cofactor and electrode.

27 Claims, 5 Drawing Sheets

OTHER PUBLICATIONS

Brune et al, "Direct, Real-Time Measurement of Rapid Inorganic Phosphate Release Using a Novel Fluorescent Probe and its Application to Actomyosin Subfragment 1 ATPase", Biochemistry 33(27):8262-8271 (1994).

Marvin and Hellinga, "Engineering Biosensors by Introducing Fluorescent Allosteric Signal Transducers: Construction of a Novel Glucose Sensor", J. Amer. Chem. Soc. 120(1): 7-11 (1998).

Drueckhammer, "New approaches to fluorescence based glucose sensors", Database FEDRIP on Dialog, NTIS, 00313296, Identifying No. 1R21DK55234-01, Abstract (1998).

Rao, "Protein engineered glucose sensor", Database REDRIP on Dialog, NTIS, 00352410, Identifying No. 1R01RR14170-01, Abstract (1998).

Careaga et al, "Large Amplitude Twisting Motions of an Interdomain Hinge: A Disulfide Trapping Study of the Galactose-Glucose Binding Protein", Biochemistry 34: 3048-3055 (1995).

Vyas et al, "Crystallographic Analysis of the Epimeric and Anomeric Specificity of the Periplasmic Transport/Chemosensory Protein Receptor for D-Glucose and D-Galactose", Biochemistry 33:4762-4768 (1994).

Rougier et al, "Use of Lectin To Detect The Sugar Components of Maize Root Cap Slime", J. Histochem Cytochem 27(4):878-881 (1979)—Abstract Biosis No.: 000068056576.

Boos et al, "Transport Properties of the Galactose-binding Protein of *Escherichia coli*", The Journal of Biological Chemistry 247(3):917-924 (1972).

* cited by examiner

BIOSENSOR

This application claims priority from Provisional Application No. 60/315,036, filed Aug. 28, 2001, the entire content of which is incorporated herein by reference.

TECHNICAL FIELD

The present invention relates, in general, to biosensors and, in particular, to bioelectronic sensors and methods of using same in analyte detection.

BACKGROUND

Chemoresponsive sensors have numerous medical, environmental, and defense applications (Ramsay (ed.) Commercial Biosensors: Applications to Clinical, Bioprocess, and Environmental Samples (John Wiley & Sons, New York (1998)). One of the main challenges in sensor development is devising materials combining analyte binding diversity with mechanisms that transduce molecular recognition events (Ellis et al, Chem. Rev. 100:2477–2478 (2000), Hellinga et al, Trends Biotechnol. 16:183–189 (1998)). Bioelectronic interfaces (Wilner et al, Agnew. Chem. mt. Ed 39:1180–1218 (2000), Ottovaleitmannova et al, Frog. Surf Sci. 41:337–445 (1992), Gopel, Biosensors Bioelect. 10:35–59 (1995)) provide a potentially powerful approach for the development of such devices. These consist of chimeric materials in which a biological macromolecule is assembled on a conducting support, and ligand binding is coupled to an electronic response (Heller, J. Phys. Chem. 96:3579–3587 (1992), Birge et al, J. Phys. Chem. B 103: 10746–10766 (1999), Katz et al, Angew Chem. mt. Ed 37:3253–3256 (1998), Wilner et al, J. Am. Chem. Soc. 121:6455–6468 (1999)). Few successful bioelectronic sensors have been developed (Boon et al, Nat. Biotechnol. 18:1096–1100 (2000), Cornell et al, Nature 387:580–583 (1997)), however, because most proteins lack the functionalities to establish ligand-mediated electronic communication.

Proteins that allosterically link the behavior of two different sites do so via conformational coupling mechanisms (Perutz, Mechanisms of Cooperativity and Allosteric Regulation in Proteins (Cambridge University Press, Cambridge) 1990). In such proteins, two sites are thermodynamically coupled when each adopts multiple, distinct local conformations that correspond to distinct global protein conformations. Such global conformational changes often correspond to different quarternary states in multimeric assemblies (Gerstein et al, Biochemistry 33:6739 (1994)) but may also involve motions such as ligand-induced hinge-bending motions (Gerstein et al, Biochemistry 33:6739 (1994)) within monomers. Such motions are found in many proteins (Gerstein et al, Biochemistry 33:6739 (1994)) and are common to all structurally characterized members of the bacterial periplasmic binding protein (bPBP) superfamily (Tam et al, Microbiol. Rev. 57:320–346 (1993)). These proteins have similar overall structures consisting of a single chain that folds into two domains linked by a hinge region (Fukami-Kobayashi et al, J. Md. Biol. 286:279–290 (1999), Quiocho et al, Mol. Microbiol. 20:17–25 (1996)).

The present invention results, at least in part, from studies demonstrating that it is possible to couple ligand binding in bPBPs to modulation of the interactions between a redox reporter group and a modified electrode surface. This scheme is analogous to ligand-dependent allosteric control of intermolecular macromolecular associations as observed in electron transport chains (Georgiadis et al, Science 257: 1653 (1992); Iwata et al, Science 281:64 (1998)) and provides the basis for powerful bioelectronic sensors.

SUMMARY OF THE INVENTION

The present invention relates, in general, to biosensors. More specifically, the invention relates to bioelectronic sensors and to methods of using such sensors in analyte detection.

Objects and advantages of the present invention will be clear from the description that follows.

BRIEF DESCRIPTION OF THE DRAWINGS

FIG. 1A. Maltose binding protein (MBP), showing the ligand-induced conformational change, FIG. 1B. glucose binding protein (GBP), FIG. 1C. glutamine binding protein (QBP) and FIG. 1D. a mutant of MBP reengineered to bind Zn(II) (eZBP). Ligands are shown as CPK representations. The attachment sites of the synthetic Ru(II) redox cofactor are indicated by large gray spheres; the C-termini by white spheres. All molecular graphics were generated with Molscript (Kraulis, Appl. Crystallorg. 24:946–950 (1991)).

FIG. 4A. G174C-MBP (1 kHz; $^eK_d$ (maltose)=4 $\mu$M; $^fK_d$(maltose)=1 $\mu$M), FIG. 4B. L255C-GBP (0.1 kHz; $^eK_d$(glucose)=2.0 $\mu$M; $^fK_d$(glucose)=0.4 $\mu$M), FIG. 4C. G174C-eZBP, a redesigned variant of MBP that binds zinc (1 kHz; $^eK_d$(zinc)=10 $\mu$M; $^fK_d$(zinc)=3 $\mu$M), FIG. 4D. E163C-QBP (0.16 kHz; $^eK_d$(glutamine)=1.0 $\mu$M; $^fK_d$(glutamine)=0.2 $\mu$M. Two binding constants are reported: $^eK_d$ is dissociation constant of the assembly, determined electrochemically; $^fK_d$ is the dissocation constant of the protein free in solution, determined by measuring changes in the intrinsic tryptophan fluorescence of the conjugates. (For every protein presented, the ligand-binding affinities determined electrochemically using a disk gold electrode are 2–5 fold weaker than those in solution. However, if a gold microelectrode prepared by flame annealing a gold wire (Creager et al, Anal. Chem. 70:4257 (1998)) is used instead of a gold disk electrode, the electrochemically determined affinities are similar to the solution affinities. This indicates that the atomic structure of the gold electrode surface is an important contributor to the interactions between the electrode and the protein.) Fractional saturation curves were obtained by fitting the baseline-corrected ac currents observed (filled circles, average of at least three determinations; error bars are smaller than the symbol) at different ligand concentrations to a standard binding isotherm (Marvin, et al, Proc. Natl. Acad. Sci. USA 94:4366–4371 (1997)).

DETAILED DESCRIPTION OF THE INVENTION

Figure 1:
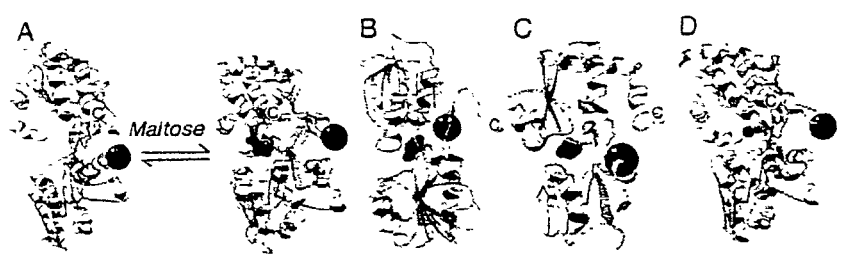
FIGS. 1A–1D. Members of the periplasmic binding protein superfamily used in this study.

The present invention relates to biosensors that use ligand-mediated macromolecular structural changes to link molecular recognition and signal transduction, the sites for these two functions being sterically separated. The present invention results, at least in part, from the realization that protein allosteric interactions can be engineered to transduce ligand (analyte) binding into detectable signals. Biosensors of the invention (e.g., comprising a derivatized chemoresponsive electrode) can be used to precisely and accurately sense a diverse set of analytes having numerous medical, environmental and defense applications (Willner et al, Angew. Chem. Int. Ed. 39:1180 (2000), Laval et al, Analyst 125:29 (2000), Lowe, Curr. Op. Chem. Biol. 10:428 (2000) and Hellinga et al, Trends Biotech. 16:1983 (1998)).

The biosensor of the invention comprises:

(i) a multilayer substrate comprising a conducting or semiconducting layer (electrode) and a self-assembled monolayer (SAM) directly or indirectly bound to the conducting or semiconducting layer;

(ii) protein molecules bound to the conducting or semiconducting layer of the multilayer substrate, through binding with the self-assembled monolayer, via a tether, e.g., a peptide, nucleic acid (e.g. DNA), or other organic molecule tether, advantageously, via a peptide tether;

(iii) a redox reporter linked to the molecules of the protein so that the reporter is positioned between the protein and the SAM; and (iv) a means for measuring a voltage or current generated by interaction between the reporter and the electrode.

The conductive layer of the present biosensor can be any conducting or semiconducting substance in any form. Examples of suitable forms include foils, wires, wafers, chips, micro- or nano-particles, semiconductor devices and coatings deposited by any known deposition process. Gold, silver, and copper conductive layers chemisorb thiol, sulfide or disulfide functional compounds, while other conductive layers can chemisorb these or other SAM-forming compounds (that include oxygen-containing compounds for etched silicon [SiH] and silicon-derivative compounds [trichiorosilanes, trimethoxysilanes, for example] for metal oxides). Preferred conductive materials include gold, silver, copper, aluminum, platinum, iridium, palladium, rhodium, mercury, silicon, osmium, ruthenium, gallium arsenide, indium phosphide, mercury, cadmium telluride, carbon and the like. Gold, silver, aluminum foil, and doped silicon wafers are particularly preferred.

The "self-assembled monolayer" (SAM) comprises a type of molecule that can bind or interact spontaneously or otherwise with a metal, metal oxide, glass, quartz or modified polymer surface in order to form a chemisorbed monolayer. A SAM is formed from molecules that bond with the surface upon their direct contact from solvent, vapor, spray or otherwise. A SAM possesses a molecular thickness, ideally, no thicker than the length of the longest molecule used therein. Molecules making up SAMs can include a functional group that adheres to the conductive layer and further can include a pendant moiety that can interact with the protein molecule to be anchored above the SAM. The SAM can pacify the electrode, that is, can reduce denaturation of the protein molecule and/or fouling of the electrode. The biosensor can also be constructed without the use of a SAM (e.g., by direct physical absorption of the protein molecules to the conducting or semiconducting layer). The biosensor can also be constructed such that the protein is not bound to the electrode (e.g., either directly (with or without tether) or via a SAM).

The biosensor can employ any protein that undergoes a conformational change upon binding to a ligand (analyte). The nature of the protein used is dependent upon the analyte to be detected. Examples of proteins suitable for use in the invention include members of the periplasmic-binding protein superfamily such as glucose-binding protein, maltose-binding protein, ribose-binding protein, arabinose-binding protein, histidine-binding protein, glutamine-binding protein. The ligand-binding sites can be naturally evolved, or engineered using rational design or directed evolution, and therefore interact with natural or non-natural ligands. Periplasmic binding proteins of E. coli: MBP, GBP, QBP and engineered versions thereof (e.g., ZBP) are merely examples, as are all homologues, analogues and/or paralogues of members of this superfamily. Other examples include hexokinase, phosphofructokinase, DNA polymerase, etc.

The redox reporter can be a redox-active metal center or a redox-active organic molecule. It can be a natural organic cofactor such as NAD, NADP, FAD or a natural metal center such as Blue Copper, iron-sulfur clusters, or heme, or a synthetic center such as an organometallic compound such as a ruthenium complex, organic ligand such as a quinone, or an engineered metal center introduced into the protein or engineered organic cofactor binding site. Cofactor-binding sites can be engineered using rational design or directed evolution techniques. The redox reporter can be bound covalently or non-covalently to the protein, either by site-specific or adventitious interactions between the cofactor and protein. It can be intrinsic to the protein such as a metal center (natural or engineered) or natural organic (NAD, NADP, FAD) or organometallic cofactor (heme), or extrinsic (such as a covalently coupled synthetic organometallic cluster). The redox reporter can be, for example, linked (e.g., covalently) to a residue on the protein surface.

The redox reporter can be a metal-containing group (e.g., a transition metal-containing group) that is capable of reversibly or semi-reversibly transferring one or more electrons. A number of possible transition metal-containing reporter groups can be used. Advantageously, the reporter group has a redox potential in the potential window below that subject to interference by molecular oxygen and has a functional group suitable for covalent coupling to the protein (e.g., thiol-reactive functionalities such as maleimides or iodoacetamide for coupling to unique cysteine residues in the protein). The metal of the reporter group should be substitutionally insert in either reduced or oxidized states (i.e., advantageously, exogenous groups do not form adventitious bonds with the reporter group). The reporter group can be capable of undergoing an amperometric or potentiometric change in response to ligand binding. In a preferred embodiment, the reporter group is water soluble, is capable of site-specific coupling to a protein (e.g., via a thiol-reactive functional group on the reporter group that reacts with a unique cysteine in the protein), and undergoes a potentiometric response upon ligand binding. Suitable transition metals for use in the invention include, but are not limited to, copper (Cu), cobalt (Co), palladium (Pd), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). That is, the first series of transition metals, the platinum metals (Ru, Rh, Pd, Os, Ir and Pt), along with Fe, Re, W. Mo and Tc, are preferred. Particularly preferred are metals that do not change the number of coordination sites upon a change in oxidation state, including ruthenium, osmium, iron, platinum and palladium, with ruthenium being especially preferred.

The reporter group can be present in the biosensor as a covalent conjugate with the protein or it can be a metal center that forms part of the protein matrix (for instance, a redox center such as iron-sulfur clusters, heme, Blue copper, the electrochemical properties of which are sensitive to its local environment). Alternatively, the reporter group can be present as a fusion between the protein and a metal binding domain (for instance, a small redox-active protein such as a cytochrome). Preferably, the reporter group is covalently conjugated to the protein via a maleimide functional group bound to a cysteine (thiol) on the protein. In any case, the reporter group is attached to the protein so that it is located between the protein and the electrode.

The protein of the biosensor can be attached to the SAM, or directly to the conductive layer, via a tether, for example, a tether comprising a peptide, nucleic acid, lipid or carbohydrate. Advantageously, the tether should be as short as synthetically feasible and site-specifically attached to the protein. In a preferred embodiment, linkage is between a C- or N-terminal oligohistidine fusion peptide (5–10 histidines), binding via immobilized metal affinity interactions (Thomson et al, Biophys. J. 76:1024 (1999)), alternatively, a cysteine to a thiol-reactive surface (Rao et al, Mikrochimica Acta 128:127–143 (1998)). The protein can also be modified so as to contain one member of a binding pair (e.g., the protein can be biotinylated) and the surface to which it is attached can be derivatized with the other member of the binding pair (e.g., the surface can be streptavidin-derivatized) (Rao et al, Mikrochimica Acta 128:127–143 (1998)).

In operation, the biosensor of the invention can be deployed in situ to monitor continuously fluctuations in analyte, e.g., in the blood stream of a patient to monitor blood glucose, etc., in water samples to monitor for toxins, pollutants, or in a bioreactor or chemical reactor to monitor reaction progress.

Analytes detectable using the biosensors of the invention include organic and inorganic molecules, including biomolecules. The analyte can be an environmental pollutant (e.g., a pesticide, insecticide, toxin, etc.); a therapeutic molecule (e.g., a low molecular weight drug); a biomolecule (e.g., a protein or peptide, nucleic acid, lipid or carbohydrate, for example, a hormone, cytokine, membrane antigen, receptor (e.g., neuronal, hormonal, nutrient or cell surface receptor) or ligand therefor, or nutrient and/or metabolite such as glucose); a whole cell (including a procaryotic (such as pathogenic bacterium) and eucaryotic cell, including a mammalian tumor cell); a virus (including a retrovirus, herpesvirus, adenovirus, lentivirus, etc.); and a spore. A particularly preferred analyte is glucose.

It will be appreciated from a reading of the foregoing that allosteric linkage can also be engineered between ligand binding and a fluorescent response (Marvin et al, Proc. Natl. Acad. Sci. USA 94:4366–4371 (1997), Marvin et al, J. Am. Chem. Soc. 120:7–11 (1998)). Engineered conformational coupling mechanisms enable a modular protein engineering approach that permits development of either optical or electronic sensors for a given analyte (e.g., glucose) (Marvin et al, J. Am. Chem. Soc. 120:7–11 (1998)) and zinc (Choi et al, Annu. Rev. Neurosci. 21:347–375 (1998)). Sensor diversity can be generated, either by taking advantage of natural diversity within a protein superfamily, which can be readily exploited using the recent advances in genomics, or by rational design methodologies (DeGrado et al, Annu. Rev. Biochem. 68:779–819 (1999)).

Certain aspects of the invention can be described in greater detail in the non-limiting Example that follows.

EXAMPLE 1

Chemoresponsive Bioelectronic Assemblies

Experimental Details

Protein purification and labeling. Proteins were produced and labeled as previously reported (Marvin et al, Proc. Natl. Acad. Sci. USA 94:4366–4371 (1997), Marvin et al, J. Am. Chem. Soc. 120:7–11 (1998)). The thiol-reactive Ru(II) reporting group, [Ru(II)(NH$_3$)$_4$(1,10-phenanthroline-5-maleimide)] (PF$_6$) was synthesized as described (Trammell et al, Bioconjug. Chem. 12:643–647 (2001)).

SAM formation. 1-mm diameter gold disk electrodes were successively polished with 6, 3, and 1-µm diamond paste and sonicated in water for 1 min between each polishing step. SAMs (self-assembled monolayers) were constructed in a manner similar to a previously published procedure (Thomson et al, Biophys. J. 76:1024–1033 (1999)). The polished electrodes were rinsed with water and immediately incubated in a solution of 11-thiolundecanoic acid (5 mM in ethanol or acetonitrile) for 24 h. Electrodes were then activated (COOH group) by immersion in a solution of 1-(3-dimethylaminopropyl)-3ethylcarbodiimide (EDC) (1 mg/mL in 20 mM MES buffer, 100 mM NaCl, pH 6.0) for 5 min, followed by a 1-h incubation in a solution (50 mM sodium phosphate buffer, 100 mM NaCl, pH 7.8) containing aminopentanol (5 mM) and N-,N-bis-(carboxymethyl)-L-lysine hydrate (lysine-NTA) (Fluka) (0.25 mM). Finally, the lysine-NTA ligands were charged with Ni(II) by immersion of the electrodes in a solution of nickel sulfate hexahydrate (40 mM in 1 mM NaOH) for 1 h followed by rinsing in water.

Electrochemistry. All electrochemical data were collected using a combined potentiostat and galvanostat equipped with a frequency response annlyzer module (Autolab/PGSTAT3O, Eco Chemie B.V.). Experiments were performed at room temperature using a single-compartment cell with a three-electrode configuration: derivatized gold working electrode, Pt auxiliary electrode, and ultralow leakage Ag/AgCl/3M KCl reference electrode (Cypress). The electrolyte solution was 20 mM NaPO$_4$, 100 mM NaCl, pH 7.5. The electrode was incubated for 1 h in 5 μM protein solutions (in electrolyte) before making measurements. Ac voltammograms were acquired in 10 mV steps using an rms amplitude modulation of 50 mV for gold disk electrodes and 15 mV for gold ball electrodes. Ac current baselines were calculated by linear extrapolation between equidistant potentials from the observed midpoint reduction potential (~220 mV), as reported previously (Creager et al, Anal. Chem. 70:4257–4263 (1998)). A 10–15 mm resting time between scans ensured reproducibility of peak current ratios.

Determination of Ru-MBP SAM coverage. Electrode area was determined electrochemically using 0.1 M ferroene in acetonitrile with a Ag/AgCl acetonitrile non-aqueous reference electrode (BAS) in 0.1 M tetrabutylammonium perchlorate. The anodic and cathodic peak currents of the ferrocene redox couple were obtained by CV as a function of the square root of the scan rate (10 to 500 mV/s). The electrode area was calculated using a diffusion coefficient (D) of 2×10$^{-5}$ cm$^2$/S, according to the modified form of the Randles-Sevcik equation (Bard et al, Electrochemical Methods (John Wiley & Sons, New York (1980)):

$$\text{Area} = (i_{peak} * (\text{scan rate} * \Pi)^{1/2})/(n * F * D^{1/2} * [Fc]) \quad (1)$$

This area was within 10% of the geometrically estimated gold electrode area.

The quantity of electroactive protein conjugates in the monolayer was determined from the integrated current of the oxidative or reductive peaks measured in the CV of the His-tag adsorbed Ru-MBP protein. The number of electrons was calculated by dividing the integrated peak current by the scan rate (4 V/s) and the charge of an electron. This number was assumed to correspond to the number of electroactive redox cofactors and was divided by the number of available MPB binding sites on the electrode. The total possible number of MPB binding sites on the electrode is calculated as a geometrical estimate obtained by dividing the electrochemically determined electrode area by the approximate area occupied by one MBP molecule (40×60$^2$), calculated from a projection of the molecular principle axes on a plane. 10–30% of the electrode surface was estimated to be covered with electroactive MBP proteins.

Preparation of cofactor-terminated SAM. A gold electrode was polished, derivatized with thioundecanoic acid, and activated with EDC as described above. The electrode was placed in an aqueous solution (20 mM sodium phosphate buffer, 100 mM sodium chloride, pH 7.8) containing 5 mM 5-aminopentanol and 0.25 mM cysteamine (estimated as at least 95% reduced by titration with dithionitrobenzene) for 1 h. The modified electrode was then rinsed with water and placed in an aqueous solution (20 mM sodium phosphate buffer, 100 mM sodium chloride, pH 7.8) containing 5 mM [Ru(II)(NH$_3$)$_4$(1,10-phenanthroline-5-maleimide)] (PF$_6$) for 1 h. A peak potential of 240 mV vs. Ag/AgCl was observed in the ac voltammograms.

Results

Figure 2:
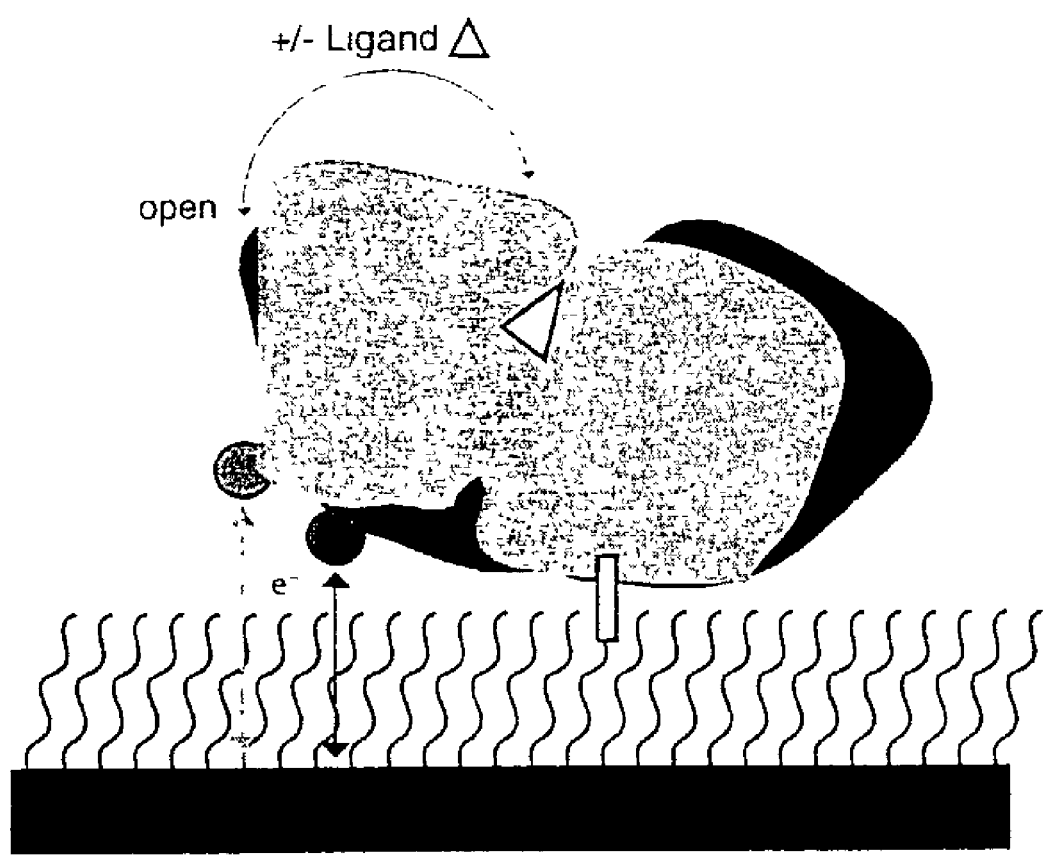
FIG. 2. Schematic illustration of the protein-mediated, ligand-dependent changes in the interactions between a Ru(II) redox reporter and a surface-modified gold electrode. Proteins were site-specifically attached through a carboxy-terminal oligohistidine peptide (rectangle) coordinated to a gold electrode modified with a self-assembled monolayer terminated with hydroxyl and Ni(II)-nitrilotriacetate headgroups. The thiol-reactive ruthenium complex (ball) was covalently linked to a mutant cysteine on the protein surface, thereby positioning the metal complex within the interface between the protein and self-assembled monolayer. Upon ligand binding (triangle), the changes in the protein conformation [open (black)→closed (grey)] alter the interaction between the cofactor and electrode surface, and therefore the observed current flowing between these two components (arrows).

Maltose-binding protein (MBP) is a structurally well-characterized member of the bPBP family (Quiocho, et al, Structure 5:997 (1997)). This protein adopts two conformations: a ligand-free open form and a liganded closed form, which inter-convert by a hinge-bending motion (FIG. 1). In order to couple ligand binding to an electrochemical response, a conformational coupling mechanism was designed to modulate the behavior of a redox reporter group. The carboxy-terminus (near the hinge-region) of MBP was tethered to the electrode, and a Ru(II) redox reporter group was conjugated site-specifically to the surface of MBP that faces the electrode (FIG. 2). This arrangement orients the ligand-binding site toward the bulk solution, and links the ligand-mediated conformational changes within the MBP-electrode interface to alterations in electronic coupling between the Ru(II) reporter group and the electrode, thereby allowing ligand binding to be measured electrochemically.

Figure 3:
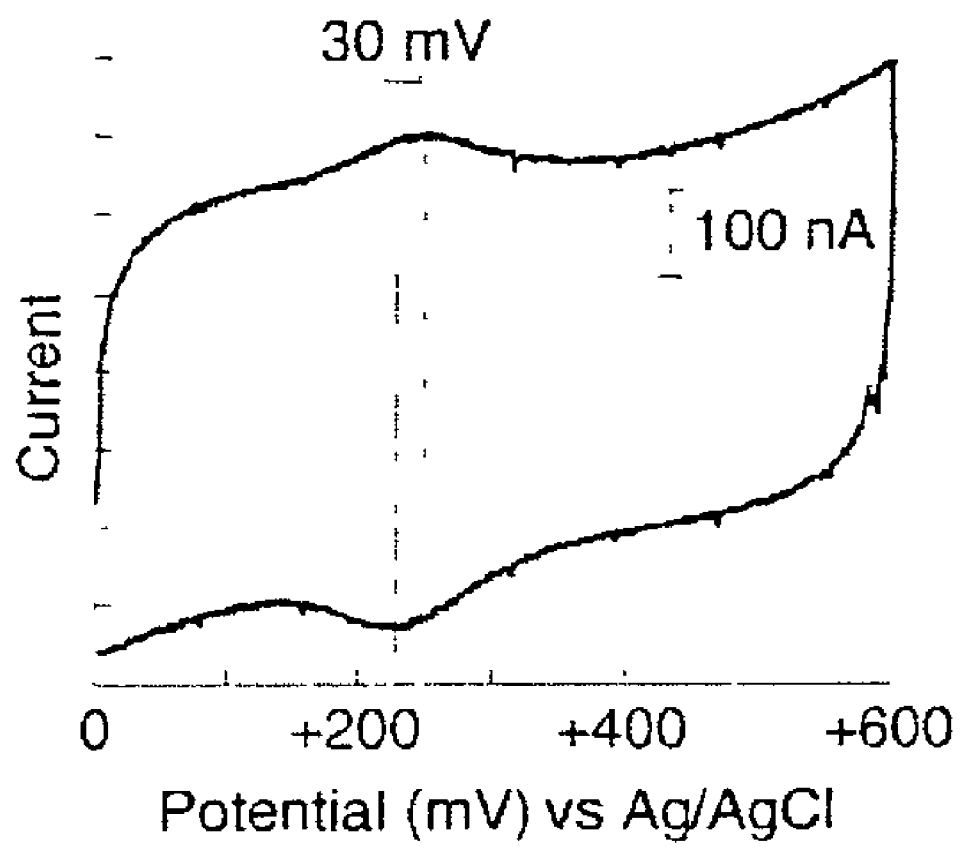
FIG. 3. Cyclic voltammogram of a Ru(II)-labelled Gly174Cys MBP mutant immobilized on a surface-modified gold electrode. The measurements were taken at a scan rate of 4V/s. The observed 30 mV peak separation is indicative of surface immobilization of the redox-active species (Bard et al, Electrochemical Methods (John Wiley & Sons, New York, (1980)). Integration of the current revealed that 10–30% of the electrode surface is covered with electroactive protein.

The presence of an electroactive protein layer on a surface-modified electrode (Thomson et al, Biophys. J. 76:1024–33 (1999)) consisting of MBP labeled with the Ru(II) cofactor at position Gly174Cys was confirmed by measuring cyclic voltammograms. At fast scan rates (4 V/s), robust, quasi-reversible cyclic voltammograms with small peak separations (~30 mV) were observed, indicative of a surface immobilized redox cofactor (Bard et al, Electrochemical Methods (John Wiley & Sons, New York, 1980)) (FIG. 3). This signal was not observed in electrodes modified with unlabeled MBP. The mid-point potential of the MBP-Ru(II) conjugate (+220 mV) is consistent with immobilization, since it is similar to the measured potential of the Ru(II) reporter directly tethered to a modified gold electrode (+240 mV) and not to that observed in the MBP-Ru(II) conjugate free in solution (+330 mV) (Trammell, et al, Bioconjug. Chem. 12:643–647 (2001)). The current observed in the cyclic voltammogram is consistent with 10%–30% coverage of the electrode surface by redox-active immobilized MBP-Ru(II) conjugates, indicating that the formation of protein multilayers is unlikely. The electrochemical signal due to the Ru(II) reporter group vanished when any one of the three tethering components (FIG. 2: His-tag, Ni(II), nitrilotriacetate groups) was omitted. Addition of a competing ligand, imidazole, also resulted in complete loss of signal. Addition of 3M guanidinium HCl followed by dilution of this protein denaturant reversibly eliminated and restored the signal. Taken together, these observations are consistent with formation of an electroactive layer consisting of a folded, electrochemically active protein conjugate, tethered to the modified electrode.

Figure 4:
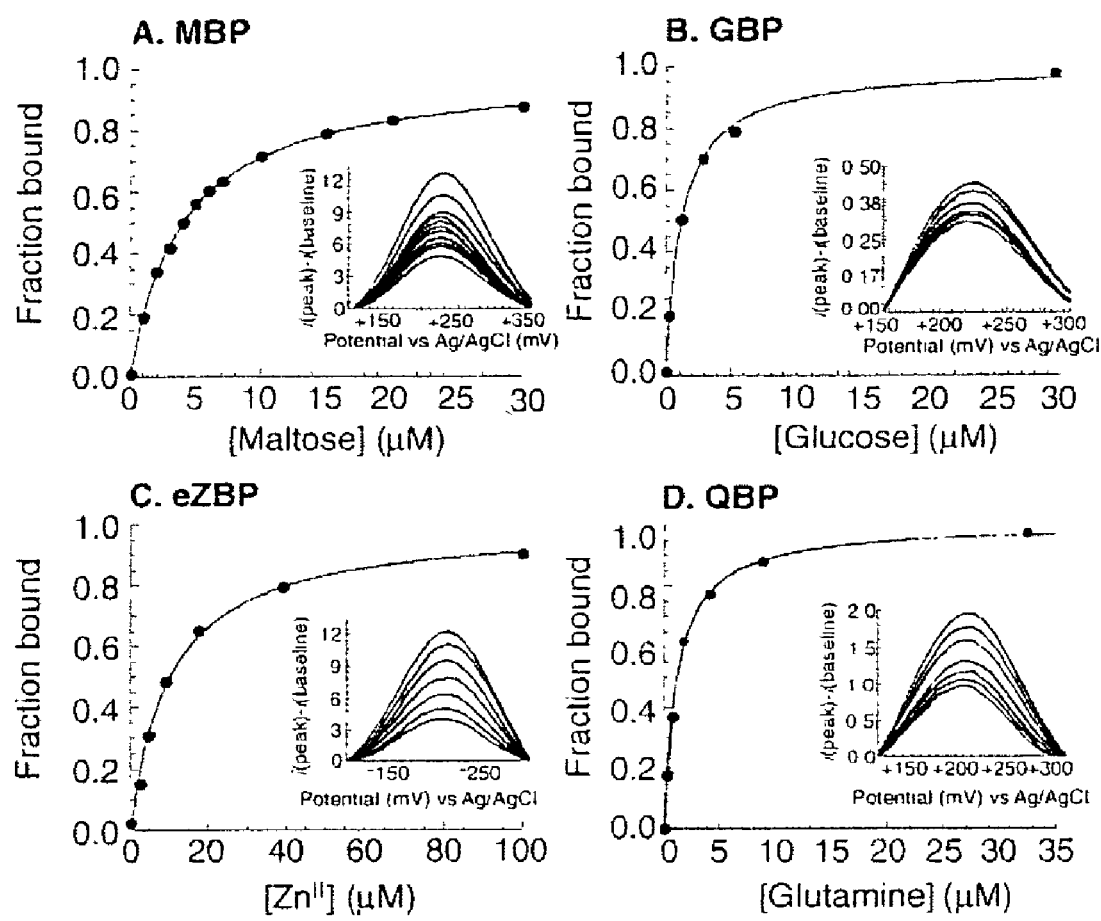
FIGS. 4A–4D. Ligand-mediated electrochemical responses of four electroactive biomolecular assemblies. Inserts show the current responses observed at different ligand concentrations, measured by scanning the potential at a constant frequency.
Figure 5:
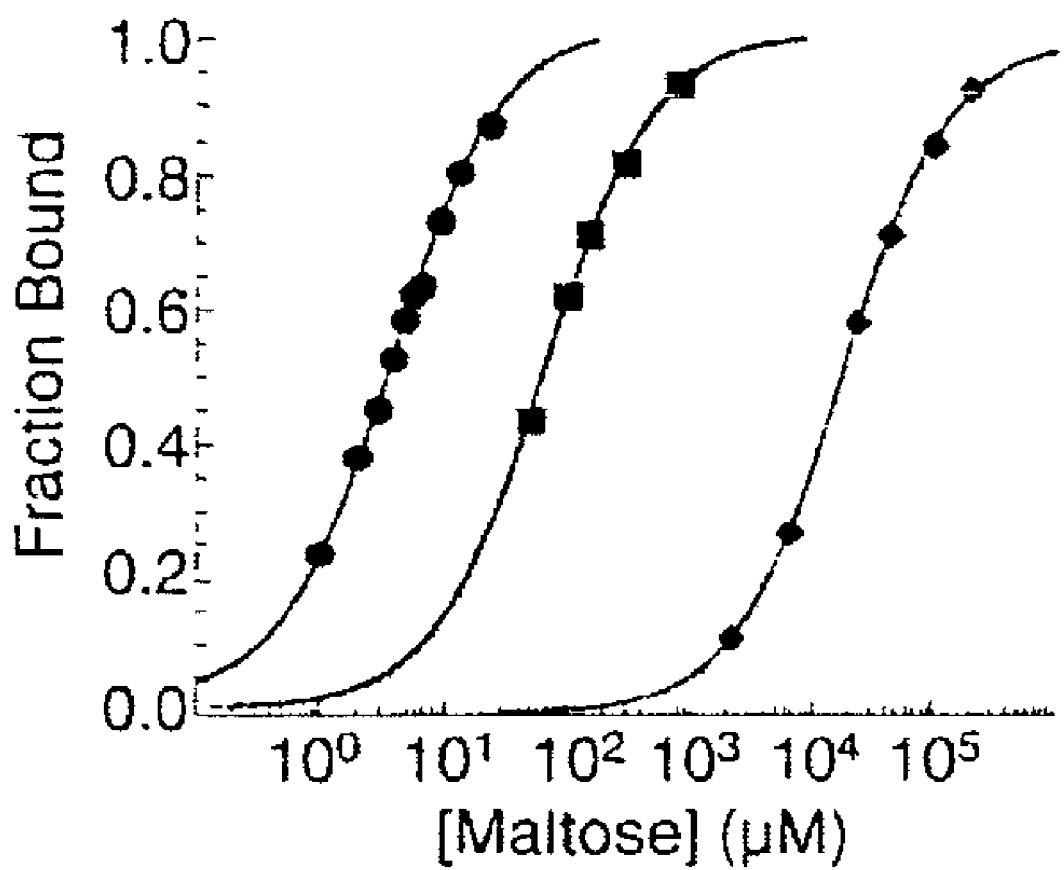
FIG. 5. Effect of maltose binding pocket mutations on maltose-dependent electrochemical responses. Ligand-dependent peak currents (filled circles, average of at least three determinations; error bars are smaller than the symbol) were fit to a binding isotherm (Marvin, et al, Proc. Natl. Acad. Sci. USA 94:4366–4371 (1997)). Circles: native MBP ($^eK_d$=4 $\mu$M; $^fK_d$=1 $\mu$M); squares, W62A MBP ($^eK_d$= 62 $\mu$M; $^fK_d$=15 $\mu$M); diamonds, W340A MBP ($^eK_d$ 18 mM; $^fK_d$= 3 mM).

The ligand dependence of the electrochemical response was probed using ac voltammetry (Bard et al, Electrochemical Methods (John Wiley & Sons, New York 1980), Creager et al, Anal. Chem. 70:4257 (1998)). The optimal ac current response due to the Ru(II) reporter group was observed at 1 kHz, and decreased from 12 to 5 μA upon addition of maltose (FIG. 4A inset). (The optimal frequency for ac voltammograms was determined using a ratio of ac peak current to baseline current (Creager et al, Anal. Chem. 70:4257 (1998)). This method is used to partially correct for capacitive contributions to the total observed current, thereby providing a relatively specific probe for the Faradaic contributions by the Ru(II) reporter group. The baseline current was linearly interpolated between the extrema of the potentiometric peak. In the single frequency potential scans currents are reported as a difference between the ac peak and baseline currents, since there is no need for frequency correction of current response.) The ligand concentration dependence of the ac current fit to a single-site binding isotherm (FIG. 4A), and only the addition of maltose (and not glucose, glutamine, or zinc) elicited an electrochemical response. Additional modified electrodes were prepared using MBP point mutants with decreased affinities for maltose (Marvin et al, Proc. Natl. Acad. Sci. USA 94:4366 (1997)). The observed maltose affinities of the resulting modified electrodes varied according to the solution binding constants of the mutant proteins (FIG. 5). All the electrochemically determined affinities correlate within a factor of four to those measured for the proteins free in solution. These observations are all consistent with a specific, ligand-mediated electrochemical response of the protein-modified electrode.

To demonstrate the generality of the use of the hinge-bending mechanism, additional chemoresponsive electrodes were constructed using two other members of the bPBP superfamily: glucose-binding protein (GBP) (Vyas et al Science 242:1290–5 (1988)), and glutamine-binding protein (QBP) (Hsiao et al, J. Mol. Biol. 262:225–242 (1996)). MBP, QBP and GBP have similar overall structures, but share little sequence homology (Tam et al, Microbiol. Rev. 57:320–346 (1993)). Even so, the GBP- and QBP-modified electrodes exhibited similar ac currents (0.5–10 $\mu$A), midpoint potentials (+220–230 mV), optimal frequencies (0.1–1 kHz), and ligand-mediated ac current changes (FIGS. 4B, 4D) as the MBP-modified electrodes. The currents decreased in response to addition of cognate ligand only (all proteins were tested with the following ligands: maltose, glucose, glutamine, glutamate, and zinc; in all cases, only addition of the cognate ligand elicited an electrochemical response), with affinities similar to those observed for protein free in solution.

Finally, a protein-modified electrode was constructed using an engineered MBP redesigned to bind Zn(II) (eZBP) (Marvin et al, Proc. Natl. Acad. Sci. USA 98(9):4955–4960 (2001)) to demonstrate that new sensors can be developed in a modular fashion by reengineering the ligand-binding site without destroying the linkage to the reporter group (Hellinga et al, Trends Biotech. 16:183–189 (1998)). The electrochemical response of the eZBP-modified electrode (FIG. 4C) was identical to wild-type MBP, but changed in response to zinc, rather than maltose.

All documents cited above are hereby incorporated in their entirety by reference.

What is claimed is:

1. A biosensor comprising:
   (i) an electrode;
   (ii) at least one molecule of a protein that undergoes a conformational change upon binding to a ligand;
   (iii) a redox reporter bound to said molecule of said protein; and
   (iv) a means for measuring a voltage or current,
   wherein said redox reporter is bound to a surface of said molecule of said protein that faces said electrode so that said redox reporter is positioned between said molecule of said protein and said electrode, and wherein the conformational change that occurs upon binding of said ligand to said molecule of said protein results in a change in the interaction between said redox reporter and said electrode that is detectable potentiometrically or amperometrically.

2. The biosensor according to claim 1 wherein said electrode comprises gold, silver, copper, aluminum, platinum, iridium, palladium, rhodium, mercury, silicon, osmium, ruthenium, gallium arsenide, indium phosphide, mercury, cadmium telluride or carbon.

3. The biosensor according to claim 1 wherein said electrode is in the form of a foil, wire, wafer, chip or micro- or nano-particle.

4. The biosensor according to claim 1 further comprising a self-assembled monolayer (SAM) bound to said electrode.

5. The biosensor according to claim 4 wherein said SAM comprises molecules comprising a functional group that adheres to said electrode.

6. The biosensor according to claim 4 wherein said SAM comprises molecules comprising a pendant moiety that interacts with said molecule of said protein.

7. The biosensor according to claim 1 wherein said protein is a genetically engineered or chemically modified protein.

8. The biosensor according to claim 7 wherein said protein is engineered to bind to a ligand other than its wild type cognate ligand.

9. The biosensor according to claim 1 wherein said redox reporter comprises a redox-active metal or a redox-active organic molecule.

10. The biosensor according to claim 9 wherein said redox reporter comprises a transition metal.

11. The biosensor according to claim 10 wherein said transition metal is selected from the group consisting of ruthenium, osmium, iron, platinum, palladium, nickel, cobalt, copper and manganese.

12. The biosensor according to claim 9 wherein the redox reporter comprises a redox-active organic molecule.

13. The biosensor according to claim 1 wherein said redox reporter comprises a functional group suitable for covalent coupling to said molecule of said protein.

14. The biosensor according to claim 1 wherein said protein is a member of the periplasmic binding protein superfamily.

15. The biosensor according to claim 14 wherein said protein is selected from the group consisting of a glucose-binding protein, maltose binding protein, ribose binding protein, arabinose-binding protein, histidine-binding protein and glutamine-binding protein.

16. The biosensor according to claim 1 wherein said molecule of said protein is bound to said electrode, or to a SAM bound to said electrode, via a tether.

17. The biosensor according to claim 16 wherein said tether comprises an organic or organo-metallic moiety.

18. The biosensor according to claim 17 wherein said tether comprises a peptide, nucleic acid, carbohydrate or lipid moiety.

19. A method for detecting the presence of, or quantifying the amount of, a ligand in a sample or system, comprising:
   contacting said biosensor according to claim 1 with said sample or system, wherein said molecule of said protein undergoes a conformational change upon binding to said ligand, and
   measuring the voltage or current generated by interaction between said redox reporter and said electrode, wherein a change in said voltage or current is indicative of the presence of, or the amount of, said ligand in said sample or system.

20. The method according to claim 19 wherein said ligand is selected from the group consisting of an environmental pollutant, a therapeutic molecule, an endogenous biomolecule, a nutrient, a cell, a virus and a spore.

21. The method according to claim 19 wherein said ligand is a biological or chemical warfare agent or an explosive.

22. The method according to claim 19 wherein said ligand is glucose.

23. The method according to claim 19 wherein said sample or system is a physiological fluid of a human or non-human patient.

24. The method according to claim 23 wherein said physiological fluid is blood, urine, sweat or cerebrospinal fluid.

25. The method according to claim 19 wherein said sample or system is a water sample or system.

26. The method according to claim 25 wherein said water sample or system is drinking water, or sea, lake, or river water, sewage, ground water or surface water.

27. The method according to claim 19 wherein said system is a bioreactor or chemical reactor.

* * * * *